(12) United States Patent
Ko et al.

(10) Patent No.: US 10,166,380 B2
(45) Date of Patent: Jan. 1, 2019

(54) IMPLANTABLE VENOUS DEVICE (71) Applicants: Po-Jen Ko, Taipei (TW); Ching-Yang Wu, New Taipei (TW); Yun-Hen Liu, Taoyuan (TW)

(72) Inventors: Po-Jen Ko, Taipei (TW); Ching-Yang Wu, New Taipei (TW); Yun-Hen Liu, Taoyuan (TW)

( * ) Notice: Subject to any disclaimer, the term of this patent is extended or adjusted under 35 U.S.C. 154(b) by 133 days.

(21) Appl. No.: 15/244,042

(22) Filed: Aug. 23, 2016

(65) Prior Publication Data
US 2016/0354593 A1  Dec. 8, 2016

Related U.S. Application Data (63) Continuation-in-part of application No. 14/616,789, filed on Feb. 9, 2015, and a continuation-in-part of (Continued)

(51) Int. Cl.
| | |
|---|---|
| *A61M 39/12* | (2006.01) |
| *A61M 39/02* | (2006.01) |
| *B29D 23/00* | (2006.01) |
| *B29K 705/08* | (2006.01) |
| *B29K 83/00* | (2006.01) |

(52) U.S. Cl.
CPC .... *A61M 39/0247* (2013.01); *A61M 39/0208* (2013.01); *B29D 23/00* (2013.01); *A61M 39/12* (2013.01); *A61M 2039/0205* (2013.01); *A61M 2039/027* (2013.01); *A61M 2039/0226* (2013.01); *A61M 2039/0235* (2013.01); *A61M 2039/0238* (2013.01); *A61M 2039/0258* (2013.01); *A61M 2039/0273* (2013.01); *B29K 2083/00* (2013.01); *B29K 2705/08* (2013.01); *Y10T 29/49963* (2015.01)

(58) Field of Classification Search
CPC .......... A61M 39/0247; A61M 39/0208; A61M 2039/027; A61M 2039/0273; A61M 2039/0258; A61M 2039/0238; A61M 2039/0235; A61M 2039/0226; A61M 2039/0205; A61M 39/12; B29D 23/00; B29K 2083/00; B29K 2705/08
USPC ..................................................... 604/288.01
See application file for complete search history.

(56) References Cited

U.S. PATENT DOCUMENTS

| | | | |
|---|---|---|---|
| 5,041,098 A * | 8/1991 | Loiterman | A61M 39/0208 604/175 |
| 5,792,104 A | 8/1998 | Speckman et al. | |

(Continued)

*Primary Examiner* — Nathan R Price
*Assistant Examiner* — Courtney Fredrickson (57) ABSTRACT

An implantable venous device includes a catheter including a passage; a locking nut including a channel for receipt of the catheter and an annular convex end; an injection seat including a base, a peripheral wall, and a mounting member projecting out of the wall; a connecting tube projecting out of the mounting member and including a bulged central portion and an annular curved outward end with the locking nut secured onto the bulged central portion; a base member including a groove; a housing including a top opening, a clamping portion on a periphery of the top opening, and a passageway through a bottom edge for receipt of the base member with the injection seat fastened in the housing, and with the locking nut in the groove; and an implant member in the top opening and including a peripheral flange urged downward by the clamping portion.

6 Claims, 8 Drawing Sheets

Related U.S. Application Data application No. 13/461,889, filed on May 2, 2012, and a continuation-in-part of application No. 12/758,087, filed on Apr. 12, 2010.

(56) References Cited

U.S. PATENT DOCUMENTS

| | | | |
|---|---|---|---|
| 6,113,572 A | 9/2000 | Gailey et al. | |
| 6,190,352 B1 | 2/2001 | Haarala et al. | |
| 6,213,973 B1* | 4/2001 | Eliasen | A61M 39/0208 604/175 |
| 6,221,064 B1 | 4/2001 | Nadal | |
| 6,290,677 B1* | 9/2001 | Arai | A61M 39/0208 604/183 |
| 8,657,795 B2* | 2/2014 | Magalich | A61M 39/0208 604/288.02 |
| 8,738,151 B2* | 5/2014 | Nelson | A61M 25/02 285/239 |
| 2005/0283118 A1* | 12/2005 | Uth | A61M 39/0208 604/175 |
| 2006/0173424 A1* | 8/2006 | Conlon | A61F 5/0056 604/288.02 |
| 2007/0233018 A1* | 10/2007 | Bizup | A61M 39/0208 604/288.01 |
| 2007/0270770 A1* | 11/2007 | Bizup | A61M 39/0208 604/288.02 |
| 2009/0216216 A1 | 8/2009 | Powers et al. | |
| 2009/0221974 A1* | 9/2009 | Paganon | A61M 39/0208 604/244 |
| 2012/0041258 A1* | 2/2012 | Jacobs | A61F 5/0056 600/37 |

* cited by examiner

IMPLANTABLE VENOUS DEVICE

CROSS-REFERENCE TO RELATED APPLICATION

This application is a continuation in part of U.S. application Ser. No. 14/616,789, filed Feb. 9, 2015, entitled "PROCESS OF MANUFACTURING TOTALLY IMPLANTABLE VENOUS DEVICE", now abandoned. The entire teachings of the above application are incorporated herein by reference.

BACKGROUND OF THE INVENTION

1. Field of Invention

The invention relates to implantable venous devices and, more particularly, to such an implantable venous device having characteristics including a housing including a clamping portion on a periphery of a top opening, an implant member in the top opening and including a peripheral flange urged downward by the clamping portion, a bottom of the implant member disposed above and parallel to a base of an injection seat to decrease a whirling motion, and an annular curved outward end of a connecting tube capable of greatly decreasing friction with an interior of a catheter. Otherwise, the catheter may be deformed.

2. Description of Related Art

Figure 7:
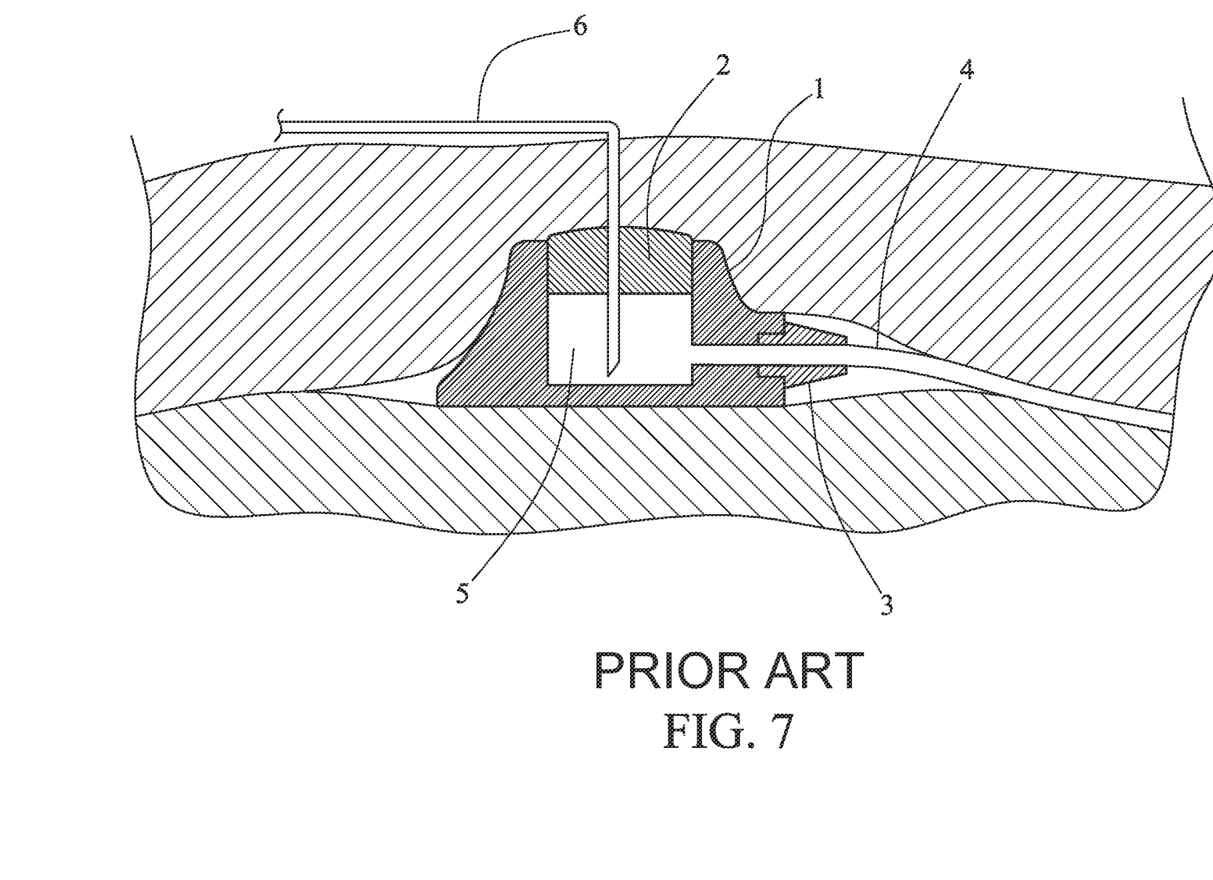
FIG. 7 is a cross-sectional view of a conventional implantable venous device.
Figure 8:
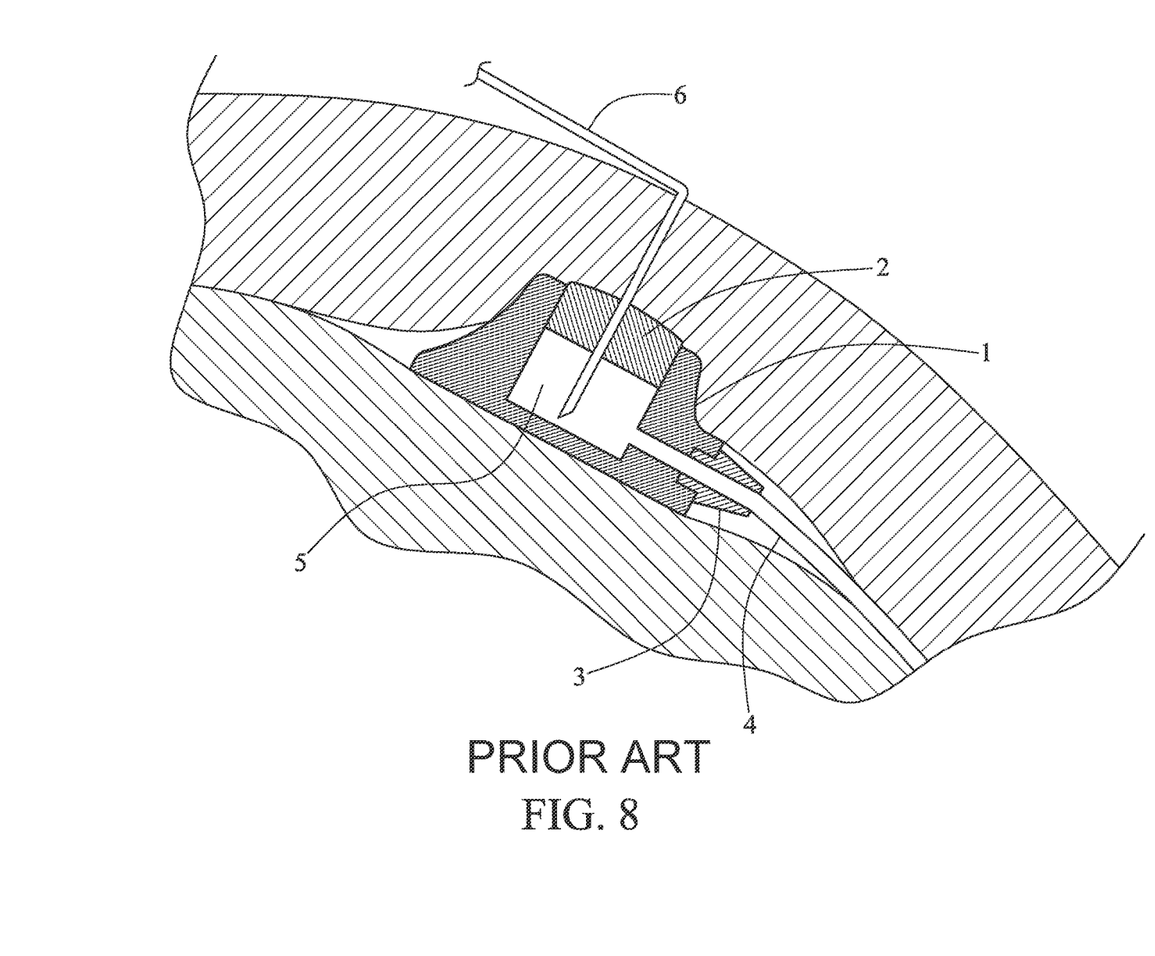
FIG. 8 is another cross-sectional view of a conventional implantable venous device.

Referring to FIGS. 7 and 8, a conventional implantable venous device comprises an implant port 1, a catheter 4, and a locking nut 3. In assembly, the catheter 4 is inserted into the connection portion of the implant port 1, and, then, the locking nut 3 is put on to fix the catheter 4. Because of the strength difference between the catheter 4 and other components, the fracture of catheter 4 may be encountered. Also, the connection portion of the catheter 4 is susceptible of fracture due to structural weaknesses. When the fracture of catheter 4 fracture occurs, the implant port 1 or the catheter 4 has to be removed because of possible fatal complications. Patients suffer from pain, and this leads to medical cost being increased.

The conventional implantable venous devices may be found to have mechanical failure because of more components. In other words, component simplification means improved performance.

Moreover, the implant port 1 of the conventional implantable venous devices is fastened in a subcutaneous pocket of the chest proximate to the armpit. However, the body is inclined. In addition, the implant port 1 of the conventional implantable venous devices has a small outer surface 2 which limits the adjustment angle of a non-coring needle 6. Also, the non-coring needle 6 is difficult to insert through the outer surface 2, via an injection chamber 5, to the catheter 4.

As shown in FIG. 7, the non-coring needle 6 is perpendicular to the implant port 1 not to the body curve. However, the inclination of the body can decrease an injectable area for the non-coring needle 6. This causes difficulties in establishing a secure venous access in obese patients. Furthermore, the non-coring needle 6 has to be inserted through the thick subcutaneous tissue among these patients and may dislodge during the patient's arm movement and may cause medication extravasation.

In an alternative approach, as shown in FIG. 8, the direction of the non-coring needle 6 is perpendicular to a tangential direction of the body surface of a patient. All of the area of the injection area could be utilized in this way, and dislodgement of the non-coring needle 6 could be further decreased. However, the dressing of this puncture method is not so convenient, because the tail of the non-coring needle 6 is not parallel to the body surface and because a Y-shape gauze needs to be placed beneath the non-coring needle 6 in order to prepare a plan for wound dressing.

Thus, a need for improvement still exists.

SUMMARY OF THE INVENTION

It is therefore an object of the invention to provide an implantable venous device comprising a catheter including a passage; a locking nut including a channel for receipt of one end of the catheter, with the channel communicating with the passage, and with an annular convex end adjacent to the catheter; an injection seat including a base, a peripheral wall on the base, a space defined by the base and the peripheral wall, a mounting member projecting out of one side of the peripheral wall with the mounting member and the peripheral wall formed integrally, and a convex portion formed at a joining portion of the mounting member and the space; a connecting tube projecting out of the mounting member and formed integrally therewith, with the connecting tube including a bulged central portion and an annular curved outward end with the locking nut secured onto the bulged central portion; a base member including a groove; a housing including a top opening, a clamping portion on a periphery of the top opening, and a passageway through a bottom edge for receipt of the base member with the injection seat fastened in the housing, and with the locking nut disposed in the groove of the base member; and an implant member disposed in the top opening and including a peripheral flange urged downward by the clamping portion, with the implant member including a bottom disposed above and parallel to the base of the injection seat.

The above and other objects, features and advantages of the invention will become apparent from the following detailed description taken with the accompanying drawings.

DETAILED DESCRIPTION OF THE INVENTION

Referring to FIGS. 1 to 6, an implantable venous device in accordance with a preferred embodiment of the invention comprises the following components as discussed in detail below.

An implant port 10 has an ergonomic shape for ease of being held by hand. The implant port 10 includes a catheter 20 having a passage 201. A locking nut 21 includes a through channel 211 for receipt of one end of the catheter 20 so that the catheter 20 is attached to a connecting tube 18. The connecting tube 18 has an internal channel 183 communicating with the passage 201. The locking nut 21 further includes an annular convex end 212 adjacent to the catheter 20.

An injection seat 17 includes an annular wall 171 of equal height provided on a disc shaped base 172 to define a space 173, a mounting member 174 projecting out of one side of the wall 171 corresponding to a connecting tube 18 and formed integrally therewith, and a convex portion 175 at a joining portion of the mounting member 174 and the space 173.

A connecting tube 18 projects out of the mounting member 174 and is formed integrally therewith. The locking nut 21 is secured onto a bulged central portion 181 of the connecting tube 18. The connecting tube 18 further includes an annular curved outward end 182. A base member 16 includes a groove 161.

A housing 11 includes a top opening 13, a clamping portion 131 on an inner surface of the housing 11, and a passageway 111 through a bottom edge for receipt of the base member 16. The injection seat 17 is fastened in the housing 11. The locking nut 21 is disposed in the groove 161. An implant member 14 is disposed in the top opening 13 and includes a peripheral flange 141 urged downward by the clamping portion 131. A bottom 142 of the implant member 14 is disposed above and parallel to the disc shaped base 172 of the injection seat 17.

The locking nut 21 tapers from the annular convex end 212 toward the other end, so that the locking nut 21 may be fastened in the groove 161. The locking nut 21 is mounted in a lower portion of the housing 11. Thus, the locking nut 21 and the catheter 20 are joined in the implant port 10. This has the benefit of preventing the joined portion of the locking nut 21 and the catheter 20 from being cracked or even broken due to stress exertion thereon.

The bulged central portion 181 has a convex shape and a diameter less than that of the channel 211. The passage 201 of the catheter 20 is securely put on the bulged central portion 181 of the connecting tube 18. This can prevent the catheter 20 from disengaging from the connecting tube 18. The annular curved outward end 182 can greatly decrease friction with an interior of the catheter 20. Otherwise, the catheter 20 may be deformed.

A distance exists between the connecting tube 18 and the disc shaped base 172 of the injection seat 17 and the convex portion 175 to be rounded outward, so that resistance and a whirling motion can be decreased. The peripheral flange 141 is urged downward by the clamping portion 131, so that the implant member 14 may withstand a predetermined pressure in an injection, and may prevent the implant member 14 from disengaging from the housing 11. The bottom 142 of the implant member 14 is disposed above and parallel to the disc shaped base 172 of the injection seat 17 to decrease a whirling motion in the space 173. The locking nut 21 and the catheter 20 are separate prior to be securely assembled to decrease steps of the manufacturing process.

Further, the catheter 20 and its locking nut 21 are formed of the same material, and, together, they are not susceptible of breaking. Moreover, the arcuate surface of the housing 11 facilitates being held by the hand in use. The disc shaped base 172 of injection seat 17 is made of metal resistant to a magnetic field (e.g., titanium alloy) or of hard plastic. Further, the disc shaped base 172 of the injection seat 17 is resistant to needle insertion and further increases the structural strength of the implant port 10. The implant member 14 is formed of silicon, so that a needle 60 can be inserted through the implant member 14 and pulled out of the implant member 14 repeatedly. Further, the needle 60 can be inserted through from one of various angles. The disc shaped base 172 is structurally strong to prevent the needle 60 from being inserted therethrough.

As a comparison, the conventional implantable venous device has a rectangular body with four edges in contact with the skin, i.e., frictional contact. This may undesirably cause erosion of the overlying skin. This is particularly true to cancer patients. Further, exposed implant ports are required to be removed or re-implanted to a new site. In the invention, the specific arcuate shape leads to less pressure and less friction between the implant port and overlying skin.

Both implantable venous devices of the prior art and the invention are secured onto the chest. The implant port 10 of the invention is different from that of the prior art. As described above, the implant port 10 has an arcuate housing 11 which has the advantages of reducing friction with the skin and of easy holding by hand.

It is noted that the locking nut 21 is mounted in the passage 201. This has the advantage of preventing the locking nut 21 from being broken due to no protection as experienced by the locking nut 21 of the conventional port. Further, the bulged central portion 181 can reduce stress generated by the assembled locking nut 21. As a result, the structural strength of the implant port 10 is greatly increased.

Figure 1:
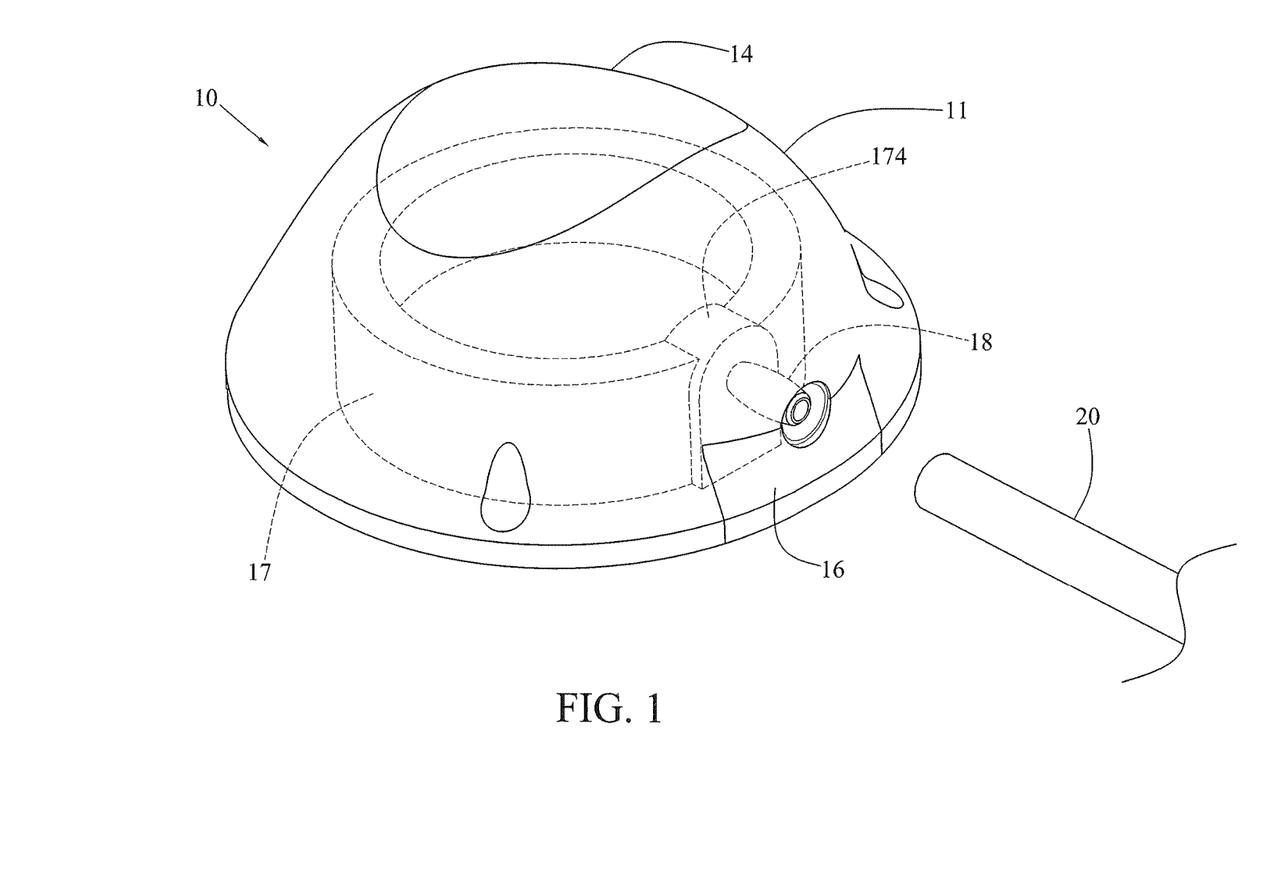
FIG. 1 is an exploded view of a preferred embodiment of an implantable venous device according to the invention.
Figure 2:
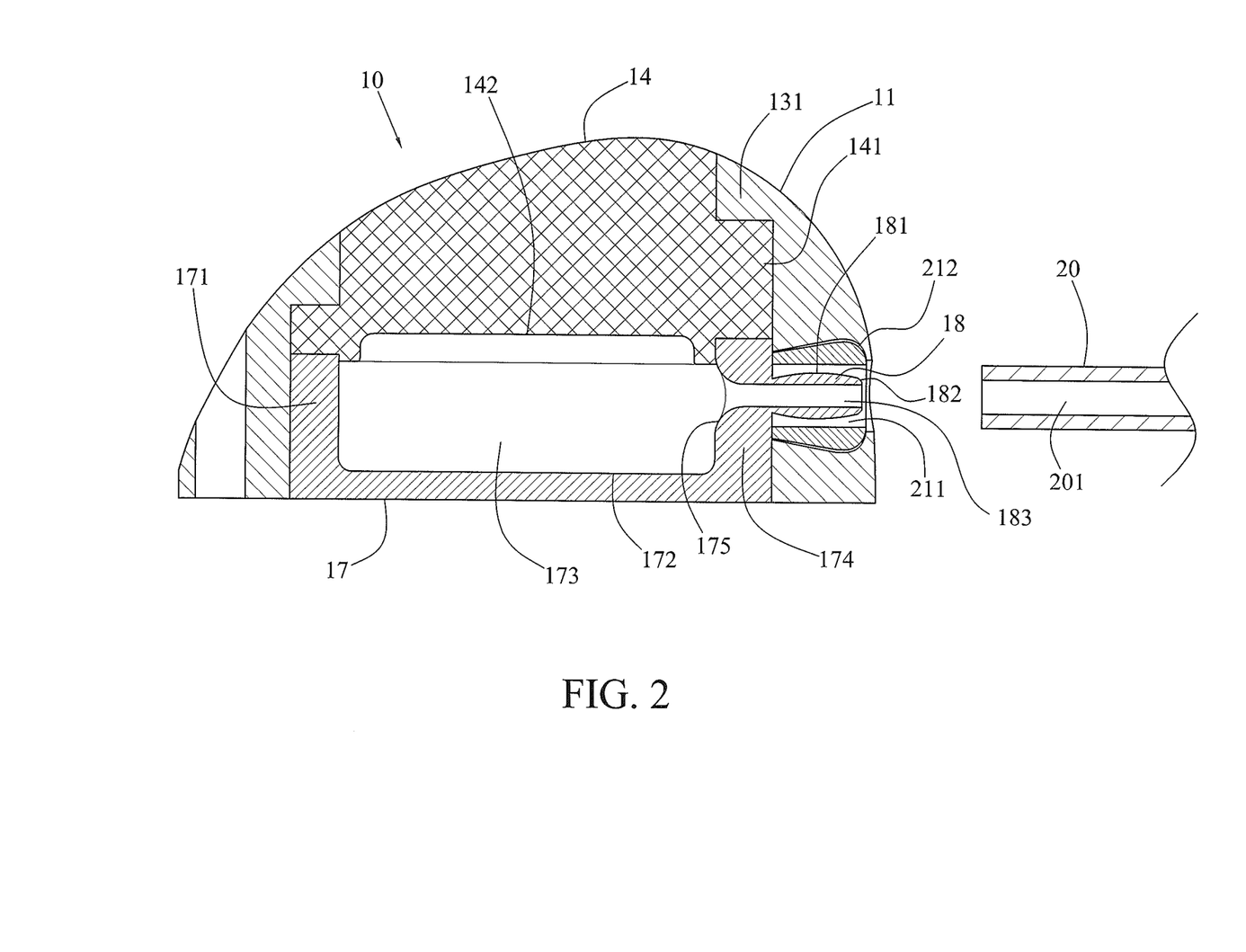
FIG. 2 is a cross-sectional exploded view of the assembled implant port.
Figure 3:
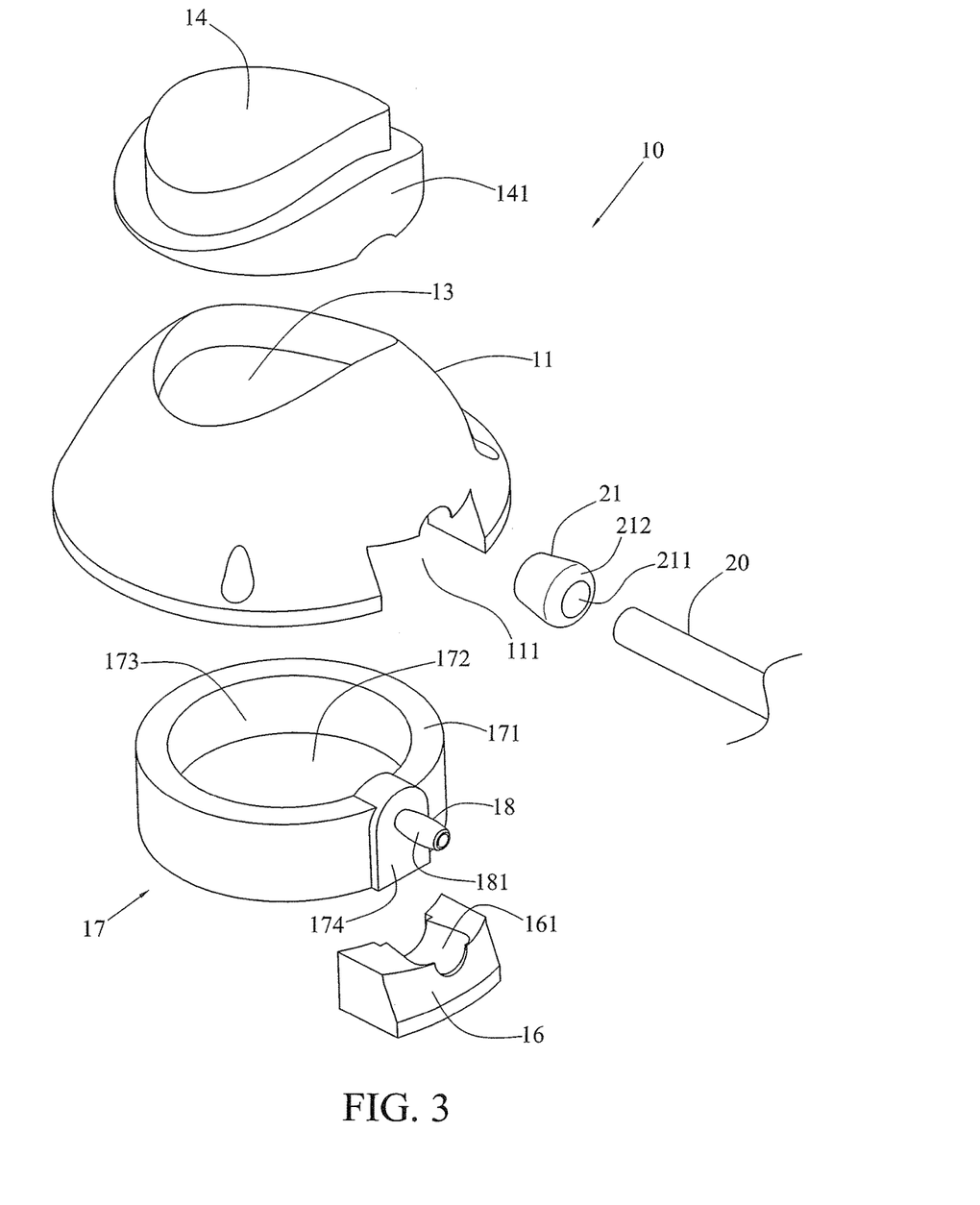
FIG. 3 is an exploded view of the implant port.
Figure 4:
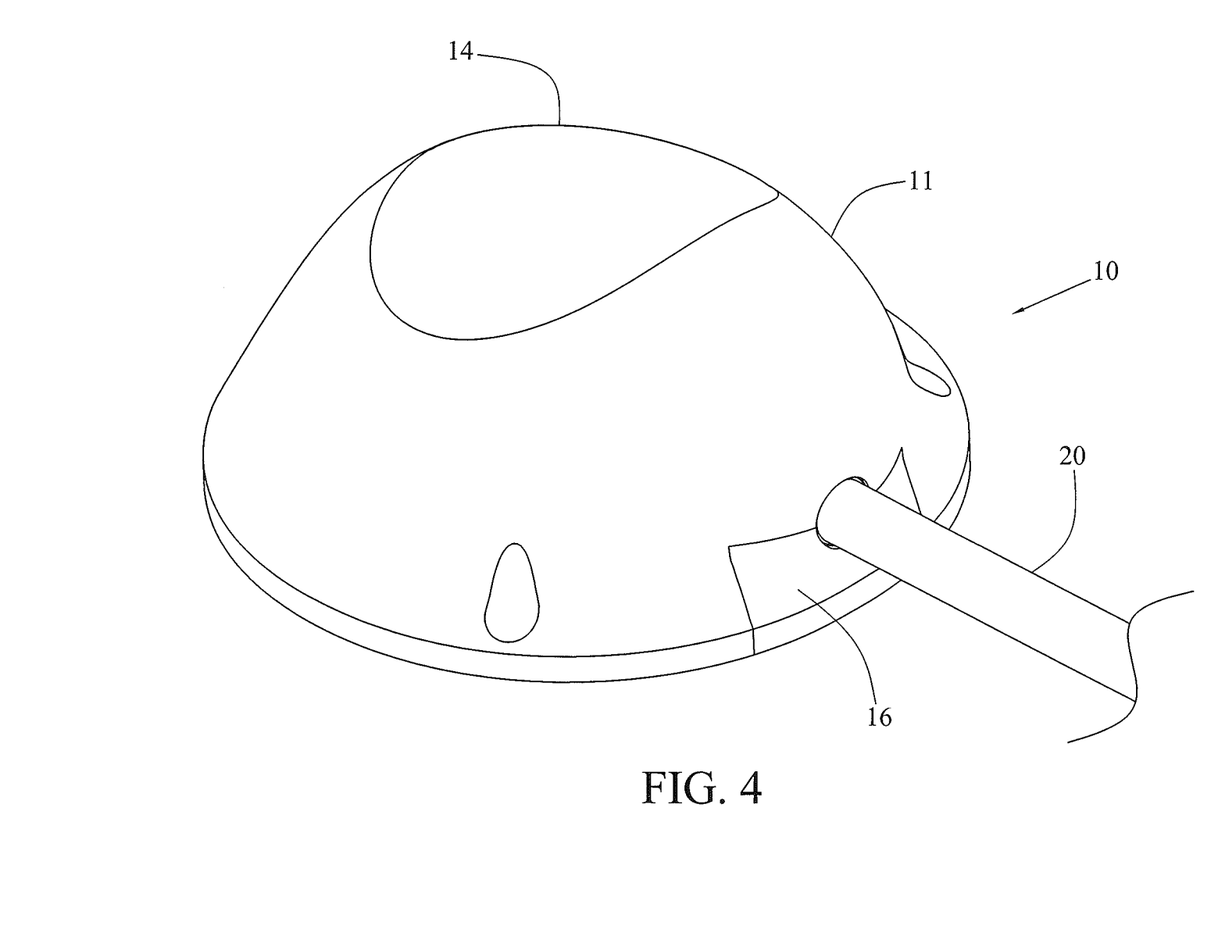
FIG. 4 is a perspective view of the assembled implant port.
Figure 5:
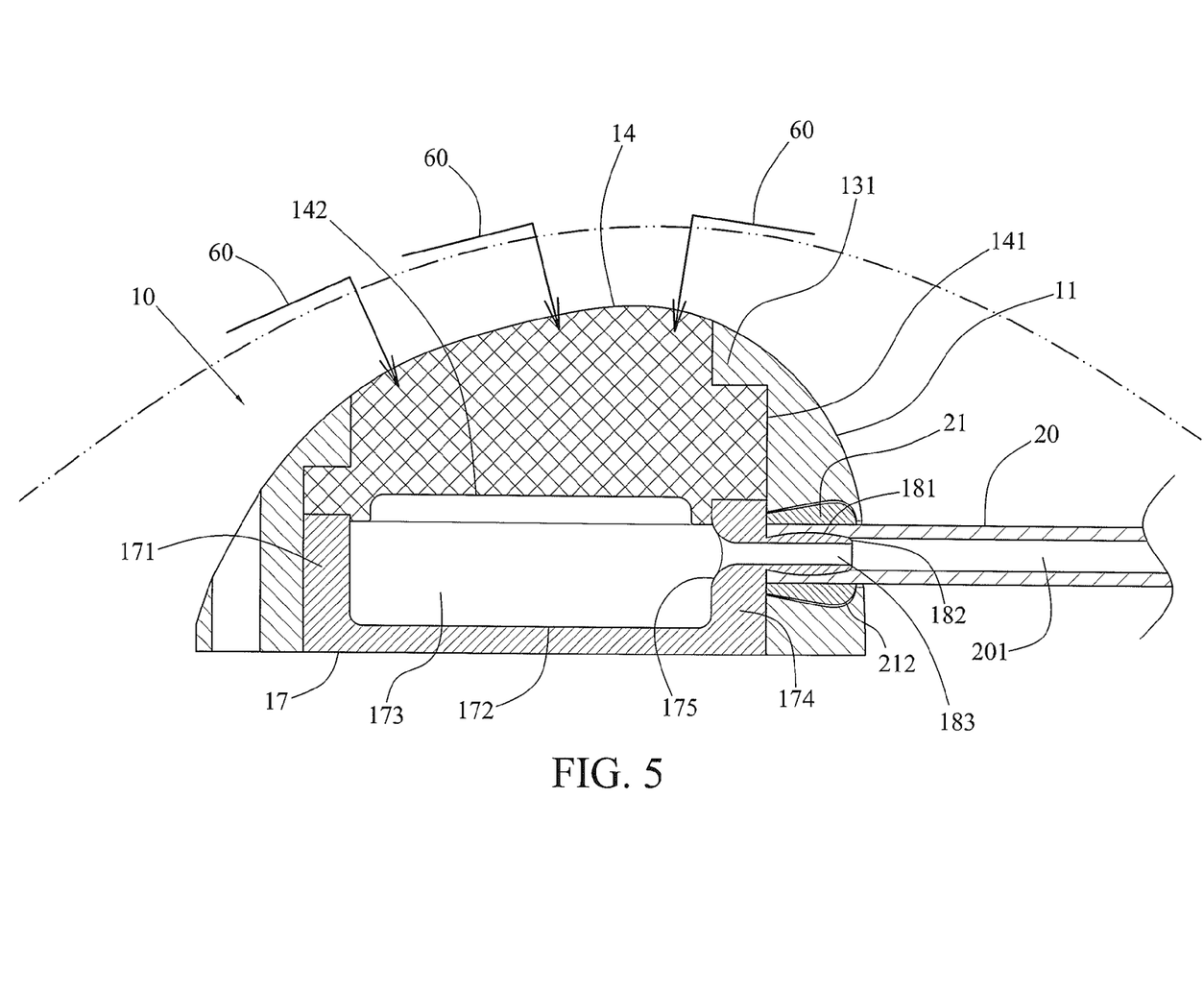
FIG. 5 is a cross-sectional view of the assembled implant port.
Figure 6:
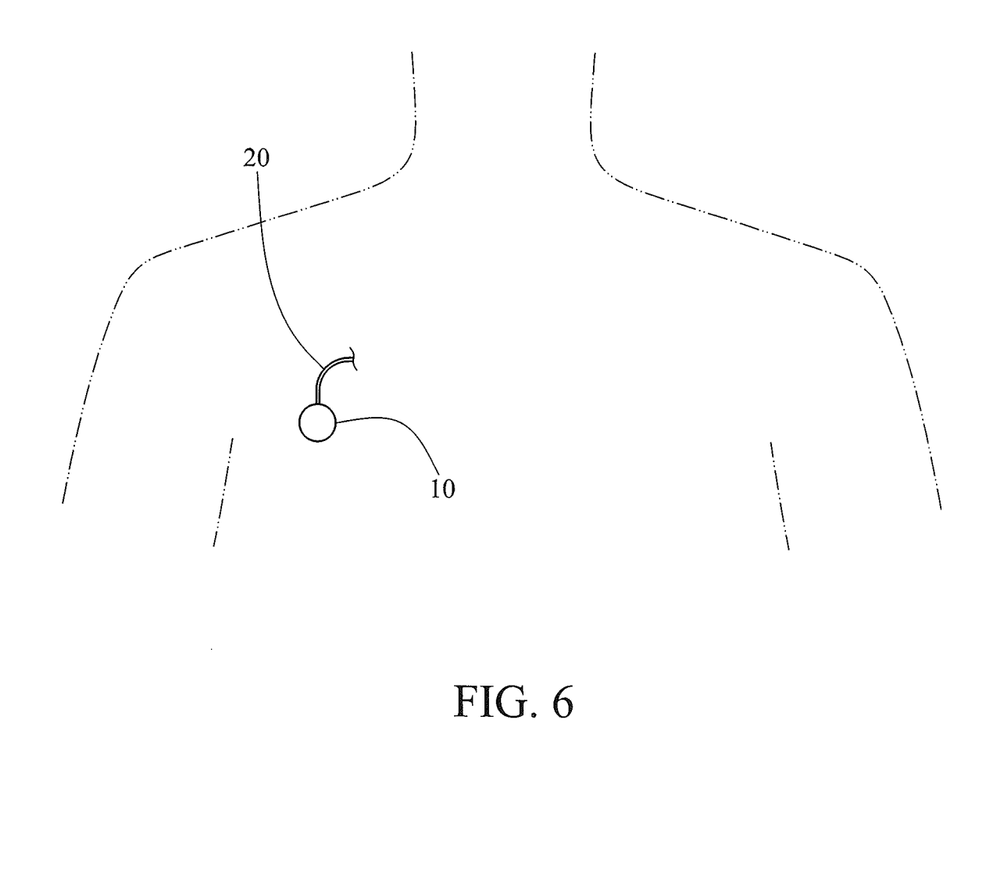
FIG. 6 is an environmental view of the implant port placed upon the body of a patient.

As shown in FIG. 5, the needle 60 can be inserted into the implant member 14 from one of various angles. The arcuate housing 11 of the implant port 10 of the invention can increase the injection area. On the contrary, the conventional implant port has a small injection area.

The portion connecting the catheter 20 to the implant port 10 is on an inner surface of the implant port 10. Hence, it is not easy to bend or even break the catheter 20. On the contrary, the conventional connection point is disposed externally of the port. Hence, it is susceptible of breaking. The catheter 20 and its locking nut 21 are formed integrally. On the contrary, the conventional catheter and its head are separate components. The connecting portion of the implant port 10 and the catheter 20 are thin to allow vibration of the catheter 20.

The implant port 10 of the invention is ergonomic in shape. Hence, it is easy to hold the implant port 10. Further, the implant member 14 facilitates the non-coring needle insertion. Furthermore, its insertion angle can be adjusted easily. In addition, the arcuate implant port 10 of the invention has less friction with the skin. The integral catheter 20 and the implant port 10 can eliminate space for the locking nut so that an area for injection can be increased. Further, the integral implant port can decrease the possibility of erroneous assembly. Furthermore, it can prevent the implant port from being adversely pressed by the catheter or even broken as experienced by the conventional catheter fastening device. In addition, it can prevent variation of assembly as experienced by the prior art.

While the invention herein disclosed has been described by way of specific embodiments, numerous modifications and variations could be made thereto by those skilled in the art without departing from the scope and spirit of the invention set forth in the claims.

What is claimed is:

1. An implantable venous device comprising:
    a catheter including a catheter end and a passage;
    a locking nut including an annular convex end and another end opposite to the annular convex end, with a channel extending from the other end to the annular convex end for receipt of the catheter, and with the annular convex end adjacent to the catheter;

an injection seat including a base, a peripheral wall on the base, a space defined by the base and the peripheral wall, and a mounting member projecting out of one side of the peripheral wall, wherein the mounting member and the peripheral wall are formed integrally, and wherein a convex portion is formed at a joining portion of the mounting member and the space;

a connecting tube projecting out of the mounting member and formed integrally therewith, with the connecting tube including a bulged central portion and an annular curved outward end, wherein the locking nut is secured onto the bulged central portion, with the catheter end and the other end abutting with the mounting member and the annular convex end spaced from the mounting member;

a base member including a groove;

a housing including a top opening, a clamping portion on an inner surface of the housing, and a passageway through a bottom edge for receipt of the base member, wherein the injection seat is fastened in the housing, and wherein the locking nut is disposed in the groove of the base member and the passageway; and an implant member disposed in the top opening and including a peripheral flange urged downward by the clamping portion, with the implant member including a bottom disposed above and parallel to the base of the injection seat.

2. The implantable venous device of claim 1, wherein the locking nut tapers from the annular convex end toward the other end.

3. The implantable venous device of claim 1, wherein the bulged central portion has a convex shape and a diameter less than that of the channel with the passage of the catheter securely put on the bulged central portion of the connecting tube.

4. The implantable venous device of claim 1, wherein the connecting tube is spaced apart from the base of the injection seat by a predetermined distance.

5. The implantable venous device of claim 1, wherein the implant member is formed of silicone, and wherein a needle is configured to be inserted through the implant member and pulled out of the implant member repeatedly.

6. The implantable venous device of claim 1, wherein a length of the groove and the passageway from the mounting member is longer than between the annular convex end and the other end with the locking nut located in the passageway of the housing and the base member.

* * * * *